(12) United States Patent
Kuenstner

(10) Patent No.: US 8,628,724 B2
(45) Date of Patent: Jan. 14, 2014

(54) INTEGRATED NEEDLE AND TEST STRIP WITH ASPIRATION APPARATUS AND METHOD OF USE

(75) Inventor: J. Todd Kuenstner, Charleston, WV (US)

(73) Assignee: Charleston Area Medical Center, Inc., Charleston, WV (US)

( * ) Notice: Subject to any disclaimer, the term of this patent is extended or adjusted under 35 U.S.C. 154(b) by 37 days.

(21) Appl. No.: 13/342,649

(22) Filed: Jan. 3, 2012

(65) Prior Publication Data
US 2013/0172704 A1 Jul. 4, 2013

(51) Int. Cl.
*A61B 5/05* (2006.01)

(52) U.S. Cl.
USPC ........... 422/82.01; 422/68.1; 422/76; 436/63; 436/65; 436/86; 436/811; 436/818; 600/372; 600/547

(58) Field of Classification Search
USPC .............. 422/68.1, 76, 82.01; 436/63, 86, 65, 436/811, 818; 600/372, 547
See application file for complete search history.

(56) References Cited

U.S. PATENT DOCUMENTS

| | | | |
|---|---|---|---|
| 5,231,993 A | 8/1993 | Haber et al. | |
| 5,377,674 A | 1/1995 | Kuestner | |
| 5,505,212 A | 4/1996 | Keljmann et al. | |
| 5,636,640 A | 6/1997 | Staehlin | |
| 5,692,503 A | 12/1997 | Kuenstner | |
| 6,393,310 B1 | 5/2002 | Kuenstner | |
| 6,602,205 B1 * | 8/2003 | Erickson et al. | 600/573 |
| 6,660,527 B2 | 12/2003 | Stroup | |
| 7,335,166 B2 | 2/2008 | Faupel et al. | |
| 8,025,628 B2 | 9/2011 | Wong et al. | |
| 2005/0015019 A1 | 1/2005 | Honda et al. | |
| 2008/0154107 A1 | 6/2008 | Jina | |
| 2010/0256524 A1 | 10/2010 | Levinson et al. | |

FOREIGN PATENT DOCUMENTS

| | | |
|---|---|---|
| WO | WO9708987 A1 | 3/1997 |
| WO | WO9710745 A1 | 3/1997 |

OTHER PUBLICATIONS

John M. Ellison, et al., "Rapid changes in postprandial blood glucose produce concentration differences at finger, forearm and thigh sampling sites," Diabetes Care, 25, No. 6: 961-964, 2002.

Zachary T. Bloomgarden, "blood glucose monitoring," Medscape Today, Oct. 13, 2003.

N.S. Oliver, et al., "Glucose sensors: a review of current and emerging technology," Diabetic Medicine, 26: 197-210, 2009.

(Continued)

*Primary Examiner* — Lyle Alexander
(74) *Attorney, Agent, or Firm* — Spilman Thomas & Battle, PLLC

(57) ABSTRACT

Methods and systems to collect a sample of bodily fluid from a patient using an integrated needle and test strip assembly are provided. In this novel assembly, the test strip and needle form one unit that captures the sample of blood or interstitial fluid from the patient once the apparatus is pressed to the skin. The hollow aspiration needle includes more than one opening at a distal end, each opening coming into contact with the bodily fluid when disposed within a cutaneous or subcutaneous layer of the patient's skin. The disclosed test strip includes at least one reaction site for testing analyte concentrations and a means for linking to many commercially available test strip meters to provide readout of the analyte concentration. The sample may be captured by capillary flow, by an integrated aspirator, or by a differential vacuum device resident on the test strip meter.

16 Claims, 10 Drawing Sheets

(56) References Cited

OTHER PUBLICATIONS

S. Kim, "A pain-free lancet with a small needle for glucose measurement," Clinical Medicine Insights: Endocrinology and diabetes, 3, 1-7, 2010.

H. Fruhstorfer and T. Mueller, "Capillary blood sampling: how much pain is necessary? Part1: Comparison of existing finger stick devices," Practical Diabetes International, vol. 12 No. 2 Mar./Apr. 1995.

John P. Bantle and William Thomas, "Glucose measurement in patients with diabetes mellitus with dermal interstitial fluid," The Journey of Laboratory and Clinical Medicine, 130, issue 4: 436-441, Oct. 1997.

Michael E. Collison, Phillip J. Stout, Tatyana S, Glushko, Kristen N. Pokela, Debra J Mullins-Hirte, Joel R. Racchini, Melissa A. Walter, Steve P. Meca, Joanna Rundquist, John J. Allen, Michael E. Hilgers and Thomas B. Hoegh, "Analytical characterization of electrochemical biosensor test strips for measurement of glucose in low-volume interstitial fluid samples," Clinical Chemistry, 45: 1665-1673, 1999.

Phillip Stout, Kristen Pokela, Debra Mullins-Hirte, Michael E. Hilgers, Ann Thorp, Michael E. Collison and Tatyana Glushko, "Site-to-site variation of glucose in interstitial fluid samples and correlation to venous plasma glucose," Clinical Chemistry 45: 1674-1675, 1999.

Suresh N, Thennadil, Jessica L. Rennert, Brain J, Wenzel, Kevin H. Hazen, Timothy L. Ruchti and Marshal B, Block, "Comparison of glucose concentration in interstitial fluid, and capillary and venous blood during rapid changes in blood glucose levels," Diabetes Technology & Therapeutics, 3, issue 3: 357-365, 2001.

David Cohen, "Painless needle copies mosquito's stinger," New Scientist, 11:38, Apr. 4, 2002; www.newscientist.com, Apr. 4, 2012.

Miyakoshi, M. Kamoi, K. Iwanaga, M. Hoshiyama, A. Yamada, A., "Comparison of patient's preference pain perception & visibility between Micro Fine Plus 31-gauge needle and microtapered Nano Pass 33-gauge needle for insulin therapy," J Diabetes Sci Technol, 1(5): 718-724, Sep. 2007.

S.A. Williams, S. Wasserman, D.W. Rawlinson, R.I. Kitney, L.H. Smaje and J.E. Tooke, "Dynamic measurement of human capillary blood pressure," Clinical Science, 74, 507-512, 1988.

\* cited by examiner

INTEGRATED NEEDLE AND TEST STRIP WITH ASPIRATION APPARATUS AND METHOD OF USE

CROSS-REFERENCE TO RELATED APPLICATIONS

Not Applicable.

STATEMENT REGARDING FEDERALLY SPONSORED RESEARCH

Not Applicable.

THE NAMES OF THE PARTIES TO A JOINT RESEARCH AGREEMENT

Not Applicable.

INCORPORATION-BY-REFERENCE OF MATERIAL ON DISC

Not Applicable.

BACKGROUND

1. Technical Field of the Invention

This invention pertains generally to an analyte test strip assembly for use in diagnostic testing for an analyte concentration. More specifically, the invention pertains to an integrated needle and test strip assembly, which may include a catheter, conduit, or aspirating chamber, and which may collect a sample of blood or interstitial fluid cutaneously or subcutaneously from a patient and, in conjunction with an analyte meter, measure an analyte concentration.

2. Background of the Invention

Electronic testing systems are commonly used to measure or identify one or more analytes in a sample. Such testing systems can be used to evaluate medical samples for diagnostic purposes and to test various non-medical samples. For example, medical diagnostic meters can provide information regarding presence, amount, or concentration of various analytes in human or animal body fluids. In addition, diagnostic test meters can be used to monitor analytes or chemical parameters in non-medical samples such as water, soil, sewage, sand, air, or any other suitable sample.

Diagnostic testing systems typically include both a test medium, such as a diagnostic test strip, and a test meter configured for use with the test medium. Suitable test media may include a combination of electrical, chemical, and/or optical components configured to provide a response indicative of the presence or concentration of an analyte to be measured. For example, some glucose test strips include electrochemical components, such as glucose specific enzymes, buffers, and one or more electrodes. The glucose specific enzymes may cause a reaction between glucose in a sample and various chemicals on a test medium, thereby producing an electrical signal that can be measured with the one or more electrodes. The test meter can then convert the electrical signal into a glucose test result.

Diagnostic testing systems have improved significantly in recent years. For example, test meters have become smaller and faster, and the amount of blood or other fluid needed to obtain accurate test results has decreased. However, although these improvements have made testing more convenient for patients, current systems have some drawbacks. For example, current systems and devices for monitoring blood glucose levels in diabetic patients require three separate devices; a lancet, a blood glucose meter, and test strips. The need to carry these three items can be inconvenient and cumbersome. In addition, carrying more components makes it easier to misplace or lose a component. Further, the current systems frequently employ lancets which can be reused. Reusing the same lancet is less sanitary than using a new, disposable lancet each time and can cause the lancet to become dull over time, leading to more pain for the patient upon use.

The pain associated with the use of a lancet is a constant concern for diabetic patients. Current lancets use a myriad of different engagement devices to create the wound. The most common method involves the use of a spring loaded lancet strike to breach the patient's skin and thereby insert the lancet. This unpleasant method has substantial drawbacks such as lancet needle movement, vibration or misapplication of force by the lancet triggering device. The overall objective of the lancet is to cause a wound that will produce blood on the surface of the skin.

Since the advent of these point of care testing systems in the 1970s ("Glucose sensors: a review of current and emerging technology," N. S. Oliver, et. al., *Diabetic Medicine*, 26:197-210, 2009; incorporated herein by reference), a noninvasive method of determining an analyte concentration such as glucose has been intensively sought and researched. To date the search has not yet resulted in a United States FDA approved device of acceptable accuracy (N. S. Oliver, et. al.). Other analytes of greater concentration have been shown to be amenable to noninvasive testing, for example, carboxyhemoglobin, as described in U.S. Pat. Nos. 5,692,503 and 6,393,310 B1, and hemoglobin, as described in U.S. Pat. No. 5,377,674 for total hemoglobin, all to this inventor. Devices are now being sold that measure these analytes noninvasively.

However, the search for a noninvasive method for the measurement of other analytes such as, for example, glucose has proven more elusive. As such, while the current methods and systems facilitate the self-monitoring of analyte concentrations in blood or bodily fluid, there is need for additional features and improvements, including systems with fewer components, less painful blood or interstitial fluid collection, more precise fluid collection methods for elderly or less dexterous patients, and less cumbersome and cleaner fluid collection methods. The present invention overcomes many of the shortcomings of the prior art of lancets and test strips.

SUMMARY

According to its major aspects, and briefly stated, the present invention includes a method and system for collection of a sample of blood or interstitial fluid from a patient using a hollow-bore mini-needle which is integrated with a test strip. Reagents on the test strip may react with an analyte in the sample, and in conjunction with an analyte meter, measure the analyte content. The sample may be aspirated through the needle to the test strip using a vacuum provided by a differential pressure device, which may be part of the integrated needle and test strip system or may be accessed via a conduit to an analyte test meter. The needle may contain one or more transverse hollow-bores allowing for more than one point of entry for the sample. Further, the needle may contact and collect sample at a subcutaneous level so that no bodily fluid is expressed to the surface of the patient's skin.

A first embodiment of the present invention is directed to a needle assembly for aspiration of a sample. The needle assembly may comprise: a needle having an upper flange, a distal end, a central hollow-bore extending through at least a portion of the needle, and at least one transverse hollow-bore in fluid communication with the central bore; and a pressure chamber having at least one port in fluid communication with the central hollow-bore of the needle. The needle assembly may be used to aspirate a sample of bodily fluid through the needle using the differential pressure created by the differential pressure chamber. The needle may pierce a subcutaneous or cutaneous layer of a patient's skin creating a channel for the bodily fluid to pass. The more efficient sample collection may permit a smaller volume of sample to be collected for analysis, which may be obtained from a smaller needle inflicted wound with consequently less pain. The methods and systems require less manual dexterity by a user and entail less pain for the user during the collection process.

The needle assembly may further comprise a needle guide having at least one port for passage of the needle; a sensor strip containing at least one reaction reagent for determining a concentration of at least one analyte in the sample, the sensor strip disposed between the differential pressure chamber and the needle guide, the sensor strip having at least one port for passage of the upper flange of the needle; and a fluid filter permeable to gas but not fluids disposed between the sensor strip and the differential pressure chamber.

The needle assembly may further comprise an analyte reaction assembly disposed between the fluid filter and the needle guide and configured to contain the sensor strip within a reaction region. The analyte reaction assembly may comprise an insulating substrate having an electrical terminal at a first end; a first conductor disposed on the insulating substrate extending from the electrical terminal to the sensor strip; a second conductor disposed on the insulating substrate extending from the electrical terminal to the sensor strip; and an insulating layer disposed on the insulating substrate, first conductor, and second conductor. In embodiments, the insulating substrate may include a void passing therethrough configured to contain the sensor strip.

In embodiments, the needle guide may further comprise an adhesive layer adjacent to the needle to impede horizontal and vertical movement of the needle assembly during use. Furthermore, the needle guide thickness may be used to determine or guide the depth of penetration of the needle during use.

In embodiments, the differential pressure chamber may be a compartment filled with a pressurized fluid and has at least one check valve. Ejection of the pressurized fluid from the compartment through the check valve may trigger a negative pressure which aspirates the sample through the needle onto the sensor strip. The pressurized fluid may be a pressurized gas. In alternative embodiments, the differential pressure chamber may be a syringe or mechanical vacuum.

In embodiments, the needle assembly for aspiration of a sample may further comprise at least one check valve positioned in the path of fluid communication between the needle and the differential pressure chamber, the check valve allowing fluid to flow in a single direction from the needle to the differential pressure chamber.

In embodiments, the needle assembly for aspiration of a sample may further comprise a protective needle cover removably disposed over the needle guide adhesive layer, the protective needle cover maintaining a sterile environment for the needle, reaction region of the analyte reaction assembly, sensor strip and needle guide.

In embodiments, the sample may comprise blood or dermal interstitial fluid. Furthermore, the needle may be about 0.2 mm to 1.0 mm in length and about 25 gauge to 35 gauge in diameter. In embodiments, the volume of the sample may be about 0.3 microliters to about 30 microliters.

In embodiments, the analyte tested using the needle assembly may be a sugar, glucose, lactate, fructosamine, glutamine, a ketone, pyruvate, 3-hydroxybutyric acid, acetyl choline, cholesterol, peroxide, a protein, prostate-specific antigen, prothrombin, hemoglobin, myoglobin, albumin, troponin, C-reactive protein, amylase, alanine transaminase, aspartate transaminase, alkaline phosphatase, creatine kinase, a peptide, brain natriuretic peptide (BNP), proBNP, a break-down product of metabolism, creatinine, bilirubin, uric acid, a hormone, luteinizing hormone, chorionic gonadotropin, thyroid stimulating hormone, a drug, an antibiotic, gentamicin, vancomycin, digitoxin, digoxin, barbiturates, methadone, amphetamine and amphetamine analogues, propoxyphene, opiates, cocaine, tetrahydrocannabinol, benzodiazepines, phencyclidine, theophylline, warfarin, a virus, a bacterium, or a coagulate. In yet further embodiments, the analyte tested may be glucose and a reaction reagent in the sensor strip may be glucose oxidase or glucose dehydrogenase.

A second embodiment of the present invention is directed to a needle and test strip assembly for collection of a sample. The needle assembly may comprise: a needle having an upper flange, a distal end, a central hollow-bore extending through the needle, and at least one transverse hollow-bore in fluid communication with the central bore; and a sensor strip containing at least one reaction reagent for determining a concentration of at least one analyte in the sample, the sensor strip having at least one port for passage of the upper flange of the needle. The needle and test strip assembly may further comprise: a needle guide having at least one port for passage of the distal end of the needle; a fluid filter permeable to gas but not fluids; and an analyte reaction assembly disposed between the fluid filter and the needle guide and configured to contain the sensor strip within a reaction region.

In embodiments, the analyte reaction assembly may comprise: an insulating substrate having an electrical terminal at a first end; a first conductor disposed on the insulating substrate extending from the electrical terminal to the sensor strip; a second conductor disposed on the insulating substrate extending from the electrical terminal to the sensor strip; and an insulating layer disposed on the insulating substrate, first conductor, and second conductor. In embodiments, the insulating substrate may include a void passing therethrough configured to contain the sensor strip.

In embodiments, the needle and test strip assembly for collection of a sample may further comprise a conduit adjacent to the fluid filter for attachment to a measurement device, which may be a vacuum pump on the analyte meter. The distal end of the needle may be in fluid communication with a differential pressure apparatus residing on the analyte meter.

A third embodiment of the present invention is directed to an integrated needle and test strip assembly which may collect a sample of blood or interstitial fluid cutaneously or subcutaneously from a patient and, in conjunction with an analyte meter, measure an analyte content. The assembly may comprise a needle having an upper flange, a distal end, a central hollow-bore extending through at least a portion of the needle, and at least one transverse hollow-bore near the distal end in fluid communication with the central bore; and a test strip containing at least one reaction reagent for determining a concentration of at least one analyte in the sample, the test strip in fluid communication with the upper flange of the needle. In embodiments, the integrated needle and test strip assembly may further comprise a pressure chamber in fluid communication with the central hollow-bore of the needle and the test strip.

A fourth embodiment of the present invention is directed to a method of using an integrated needle and test strip assembly.

The method comprises pressing the distal end and at least one transverse bore of a needle having an upper flange, a distal end, a central hollow-bore extending through at least a portion of the needle, and at least one transverse hollow-bore near the distal end in fluid communication with the central bore into skin of a patient; and holding the needle in place until a sample is drawn through the needle into a test strip in fluid communication with the needle by way of a differential pressure chamber in fluid communication with the needle and the test strip, the test strip containing at least one reaction reagent for determining a concentration of at least one analyte in the sample.

A fifth embodiment of the present invention is directed to a method of using an integrated needle and test strip assembly. The method comprises pressing the distal end and at least one transverse bore of a needle having an upper flange, a distal end, a central hollow-bore extending through at least a portion of the needle, and at least one transverse hollow-bore near the distal end in fluid communication with the central bore into skin of a patient; and immediately removing the needle from the skin, a sample having been drawn through the distal end of the needle into a test strip in fluid communication with the needle by way of a differential pressure chamber in fluid communication with the needle and the test strip, the test strip containing at least one reaction reagent for determining a concentration of at least one analyte in the sample. In embodiments of the method, the differential pressure chamber may contain a pressure that is greater than atmospheric pressure or a pressure that is less than atmospheric pressure.

BRIEF DESCRIPTION OF THE DRAWINGS

Aspects, features, benefits and advantages of the embodiments herein will be apparent with regard to the following description, appended claims, and accompanying drawings. In the following figures, like numerals represent like features in the various views. It is to be noted that features and components in these drawings, illustrating the views of embodiments of the present invention, unless stated to be otherwise, are not necessarily drawn to scale.

DETAILED DESCRIPTION

Figure 1:
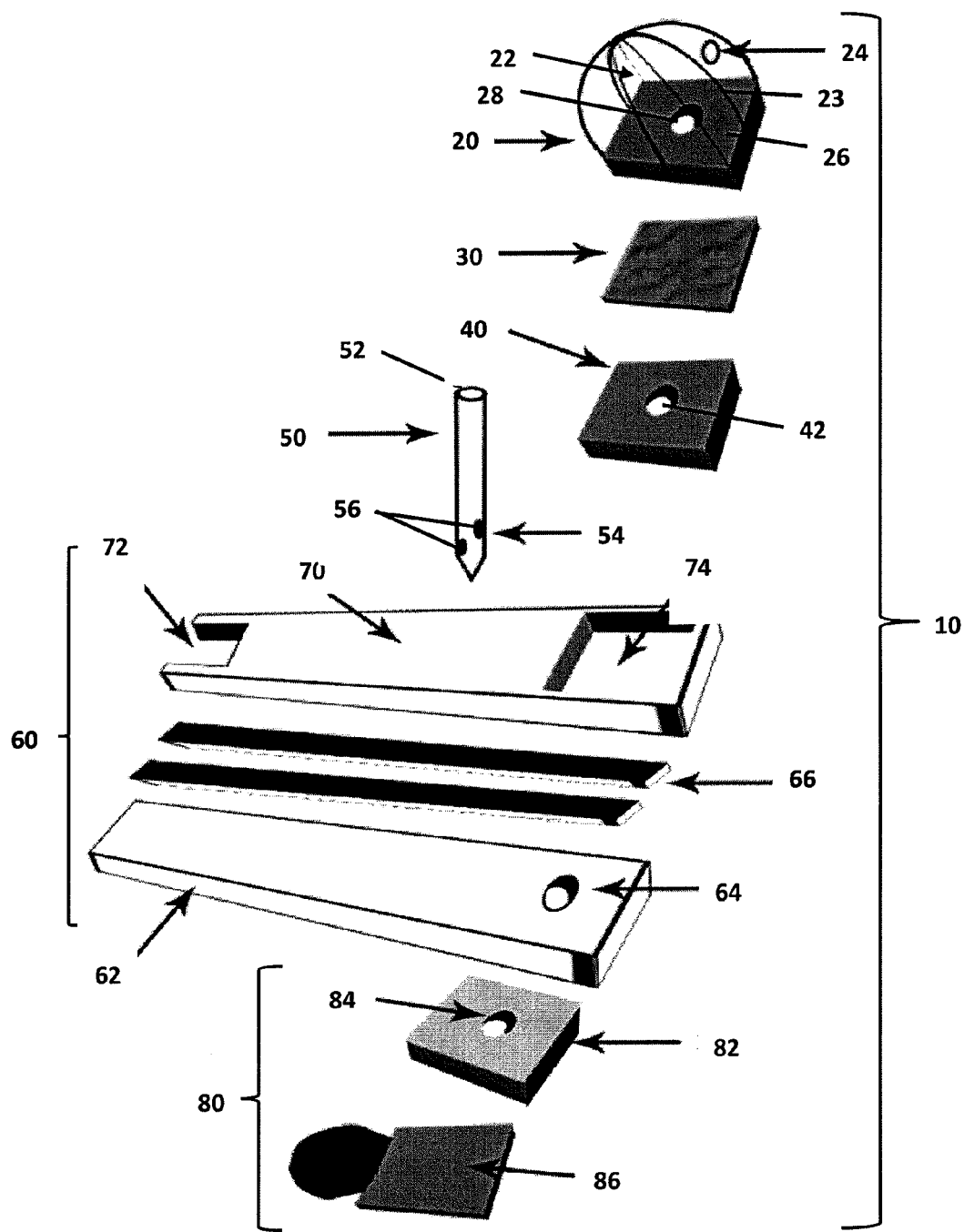
FIG. 1 illustrates an exploded view of an integrated needle and test strip assembly using a differential pressure chamber to aspirate a sample in accordance with certain aspects of the present invention.

In the following description, the present invention is set forth in the context of various alternative embodiments and implementations involving an integrated needle and test strip assembly which may allow a sample of bodily fluid from a patient to be collected and tested. The needle assembly may be used to collect a sample of blood or interstitial fluid cutaneously or subcutaneously from the patient and, in conjunction with an analyte meter, measure an analyte content of the collected blood or interstitial fluid. The sample may be aspirated onto a test region of the integrated needle and test strip assembly or may flow to the test region by capillary action. The needle assembly may provide a single needle having more than one opening at a distal end, each opening coming into contact with a bodily fluid when disposed within a cutaneous or subcutaneous layer of the patient's skin. In accordance with aspects of the present invention, the integrated needle and test strip assembly may be mated to an analyte meter configured to automatically begin the metering process as the bodily fluid is collected into the assembly.

Various aspects of the integrated needle and test strip assembly may be illustrated by describing components that are coupled, attached, and/or joined together. As used herein, the terms "coupled", "attached", and/or "joined" are interchangeably used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements shown in said examples.

Various aspects of the integrated needle and test strip assembly may be illustrated with reference to one or more exemplary implementations. As used herein, the term "exemplary" means "serving as an example, instance, or illustration," and should not necessarily be construed as preferred or advantageous over other variations of the devices, systems, or methods disclosed herein. "Optional" or "optionally" means that the subsequently described event or circumstance may or may not occur, and that the description includes instances where the event occurs and instances where it does not. In addition, the word "comprising" as used herein means "including, but not limited to".

Furthermore, throughout the specification, reference to "one embodiment," "an embodiment," or "some embodiments" means that a particular described feature, structure, or characteristic is included in at least one embodiment. Thus, appearances of the phrases "in one embodiment," "in an embodiment," or "in some embodiments" in various places throughout this specification are not necessarily all referring to the same embodiment. Those skilled in the art will recognize that the various embodiments can be practiced without one or more of the specific details or with other methods, components, materials, etc. In other instances, well-known structures, materials, or operations are not shown or not described in detail to avoid obscuring aspects of the embodiments.

Relative terms such as "lower" or "bottom" and "upper" or "top" may be used herein to describe one element's relationship to another element illustrated in the drawings. It will be understood that relative terms are intended to encompass different orientations of aspects of the integrated needle and test strip assembly in addition to the orientation depicted in the drawings. By way of example, if aspects of the integrated needle and test strip assembly shown in the drawings are turned over, elements described as being on the "bottom" side of the other elements would then be oriented on the "top" side of the other elements as shown in the relevant drawing. The term "bottom" can therefore encompass both an orientation of "bottom" and "top" depending on the particular orientation of the drawing.

It must also be noted that as used herein and in the appended claims, the singular forms "a", "an", and "the" include the plural reference unless the context clearly dictates otherwise. Thus, for example, reference to an "orifice" is a reference to one or more orifices and equivalents thereof known to those skilled in the art, and so forth. Unless defined otherwise, all technical and scientific terms used herein have the same meanings as commonly understood by one of ordinary skill in the art.

It will be appreciated that the following embodiments and implementations are illustrative and various aspects of the invention may have applicability beyond the specifically described contexts. Furthermore, it is to be understood that these embodiments and implementations are not limited to the particular components, methodologies, or protocols described, as these may vary. The terminology used in the description is for the purpose of illustrating the particular versions or embodiments only, and is not intended to limit their scope in the present disclosure which will be limited only by the appended claims.

Referring now to the drawings, embodiments of the integrated needle and test strip assembly of the present invention are shown in FIGS. 1-7 generally designated by the reference numeral 10. FIG. 1 illustrates an exploded view of an embodiment of the integrated needle and test strip assembly 10 which may include a differential pressure chamber 20, a sensor strip 40, a needle 50, an analyte reaction assembly 60, and a needle guide and protection assembly 80. The assembly 10 provides a single integrated unit that may allow a user to collect a sample by pushing the needle 50 through a barrier layer on a patient. The needle may then provide a transport channel for the sample to the sensor strip 40 for estimation of an analyte concentration using the analyte reaction assembly 60 in conjunction with a commercial test strip meter. Further, the sample may be aspirated onto the sensor strip 40 by action of the differential pressure chamber 20.

The differential pressure chamber 20 may be a differential pressure pump or a syringe, for example, or any other suitable apparatus or system for creating a pressure differential between an uppermost needle flange 52 and a distal end 54 of the needle 50. The needle 50 may be a hollow aspiration needle, for example, having a central hollow-bore extending from the distal end 54 or from near the distal end 54 to an opening in the needle flange 52. The distal end 54 of the needle 50 may be used to penetrate the barrier layer and provide a pathway for collection of a sample from beneath the barrier layer onto the sensor strip 40. For example, the needle 50 may be used to pierce a patient's skin so that a sample of blood or interstitial fluid may be collected from the distal end 54 through the central hollow-bore onto the sensor strip 40. The needle is thus serving the dual purpose of fluid sampler, or lancet, and collection channel.

This dual purpose of the needle of the present invention—fluid sampler and collection channel—simplifies the use of the integrated needle and test strip assembly 10. As discussed previously, current diagnostic test systems necessitate a separate lancet which creates a wound in the patient's skin and allows a sample of bodily fluid to pool on the surface of the skin. The pooled sample of fluid is then captured onto a test region by capillary action. Not only does this two-step system generate more sample than may be required, the sample is exposed to air and other contaminants prior to collection. The patient is left with a pool of sample, most commonly blood, which is not used for testing and must be cleaned. Furthermore, most current lancet systems use a mechanical spring loaded actuator to trigger the lancet's entry into the patient's skin. Such systems enter the skin layer rapidly, come to an abrupt stop and then quickly retract. These combined abrupt actions not only cause a significant amount of pain for the patient, but also cause the wound channel to collapse, trapping some or all of the bodily fluid beneath the skin. As a result, the patient must apply pressure to milk the sample to the surface of the skin. The needle 50 of the integrated needle and test strip assembly 10 of the present invention solves these problems.

In embodiments, the needle 50 of the integrated needle and test strip assembly 10 does not use an actuator. Rather, the needle 50 may be pressed through the barrier layer on a patient using pressure, for example, on the differential pressure chamber 20. The needle may further be held in place on the barrier layer by an adhesive on the needle guide 82 so that the wound channel remains open during sample collection.

In accordance with an aspect of the present invention, the needle 50 may be configured with at least one transverse hollow-bore 56, or orifice, in fluid communication with the central hollow-bore to assist collection of the sample onto the sensor strip 40. Such a design may provide several advantages. First, when used to collect a sample of blood or interstitial fluid, the orifice(s) 56 may, for example, prevent the sides of the needle 50 from tamponading blood flow from the capillaries, which may sometimes result if the only site of fluid collection is from a single point at the distal end of the needle 54. Second, the reduced surface area of such a needle 50 may elicit less pain to the patient when the needle 50 penetrates the skin. As noted in the article "Painless needle copies mosquito's stinger," David Cohen, *New Scientist*, 11: 38, Apr. 4, 2002, the entirety of which is incorporated herein by reference, the process of a mosquito removing blood from a human is essentially painless. The mosquito proboscis is highly serrated, thus reducing the surface area which is in contact with the human tissue and consequently reducing stimulation of the nerves. Third, the orifices 56 may increase the surface area in which blood or interstitial fluid enter the needle 50. This increased surface area may aid in more efficient sample collection and may be advantageous in the event of clotting of blood or blockage, for example, at the needle tip.

It will be appreciated that the orifice(s) 56 in such a needle 50 may be formed in any number of different patterns on the needle 50. For example, the orifice(s) 56 may be formed in a helical (spiral) pattern along the longitudinal axis of the needle 50, or may be formed in a staggered pattern where more than one orifice 56 may lie along the same longitudinal axis. Further, the number of orifice(s) 56 may be variable and may depend on a number of different parameters, including the size of the orifice(s) 56, the size of the opening at the distal end 54 of the needle 50, the intended application in terms of the makeup and location of the sample, and the volume of sample to be collected. The spacing between the orifice(s) 56 and the distance between the distal end 54 of the needle 50 and the orifice(s) 56 may vary. Thus, while FIGS. 1, 5, 6 and 10 are shown with a prescribed number, size and pattern of orifice(s) 56, this is merely for illustrative purposes and does not limit the present invention in any way. It will further be appreciated that the needle 50 can include only a single orifice 56 and may or may not include an opening that is formed at the distal tip 54.

As discussed above, the design of the needle 50 to include at least one orifice 56 may aid in more efficient sample collection and may thus allow the use of needles which have shorter lengths and smaller diameters. The needle 50 of the integrated needle and test strip assembly 10 may be between 0.2 mm and 1.0 mm in length and may be 25 gauge to 35 gauge in diameter. As noted in the article "Capillary blood sampling: how much pain is necessary? Part 1: comparison of existing finger stick devices," H. Fruhstorfer and T. Mueller, *Practical Diabetes* 12(2): 72-74, March/April 1995, the entirety of which is incorporated herein by reference, longer and thicker lancet designs, as used in conventional integrated test apparatuses, often elicit greater pain and collect an amount of blood that is too large. Clinical trials have shown that one of the smallest lancets on the market, the Tiniboy™, is less painful to use ("A pain-free lancet with a small needle for glucose measurement," S. Kim, *Clinical Medicine Insights: Endocrinology and Diabetes* 2010: 3 1-7, the entirety of which is incorporated herein by reference). The dimensions of this lancet are 36 gauge (0.18 mm in diameter) and 0.7 mm in length (see www.tiniboy.com). Current diagnostic methods for analyte determination typically require sample volumes as small as 0.5 microliters to 2.0 microliters. Thus, the design of the integrated needle and test strip assembly 10 of the present invention may permit the use of a needle 50 which has a shorter length and smaller diameter, allowing for collection of sufficient blood or interstitial fluid with a minimum of pain for the patient.

In accordance with an aspect of the present invention, the needle 50, or a portion thereof, may be coated with a lubricant or other suitable substance to reduce friction upon insertion, thus reducing the resultant discomfort and/or permitting the use of a larger bore needle if desired. As noted in the article "Comparison of patient's preference, pain perception, and usability between Micro Fine Plus 31-gauge needle and microtapered NanoPass 33-gauge needle for insulin therapy," Miyakoshi, M. et. al., *J Diabetes Sci Technol*, 1(5): 718-724, September 2007, the entirety of which is incorporated herein by reference, lubricant on the external surface of a needle may reduce discomfort during needle insertion.

In accordance with an aspect of the present invention, the sample collected using the integrated needle and test strip assembly 10 may be blood or interstitial fluid. Several published studies have shown that for a standard analyte measurement, blood and interstitial fluid showed similar results. For example, glucose measurements on interstitial fluid were practically indistinguishable from capillary blood glucose measurements (1. "Glucose measurement in patients with diabetes mellitus with dermal interstitial fluid," John P Bantle and William Thomas, *The Journal of Laboratory and Clinical Medicine*, 130, issue 4: 436-441, October, 1997. 2. "Analytical characterization of electrochemical biosensor test strips for measurement of glucose in low-volume interstitial fluid samples," Michael E. Collison, et. al., *Clinical Chemistry*, 45: 1665-1673, 1999. 3. "Site-to-site variation of glucose in interstitial fluid samples and correlation to venous plasma glucose," Phillip Stout, et. al., *Clinical Chemistry* 45: 1674-1675, 1999.), each reference being incorporated herein by reference. Further, an additional article showed that there is no time lag of glucose concentration between interstitial fluid and capillary blood ("Comparison of glucose concentration in interstitial fluid, and capillary and venous blood during rapid changes in blood glucose levels," Suresh N. Thennadil, et. al., *Diabetes Technology & Therapeutics*, 3, issue 3: 357-365, 2001; incorporated herein by reference.)

The needle 50 of the integrated needle and test strip assembly 10 of the present invention may be used to penetrate a barrier layer on a patient. In embodiments, the barrier layer is a cutaneous or subcutaneous layer of skin on the patient's body, preferably at the fingertip. As discussed above, the design of the needle 50 to include at least one orifice 56 and to be of short length (between 0.2 and 1.0 mm) and small diameter (25 to 35 gauge) allows for less painful collection of the sample. When used in the fingertip to collect a sample of blood or interstitial fluid, this provides a great advantage. While the fingertip has more nerve endings, capillary blood is more plentiful, as noted in the article "Blood glucose monitoring," Zachary T. Bloomgarden, *Medscape Today*, Oct. 13, 2003, incorporated herein by reference. Furthermore, during conditions of rapidly changing analyte concentration, there may be a time delay difference with venous blood which is evident at alternate test sites, such as the forearm or thigh for example, but is not evident with fingertip sampling of capillary blood, as discussed in the article "Rapid changes in postprandial blood glucose produce concentration differences at finger, forearm and thigh sampling sites," John M. Ellison, et. al., *Diabetes Care*, 25, number 6: 961-964, 2002, incorporated herein by reference.

In accordance with other aspects of the present invention, although referred to herein as a needle, the needle 50 may be a lancet or a combination lancet and hollow needle, having a solid portion and/or a hollow portion, or any combination thereof.

Figure 2:
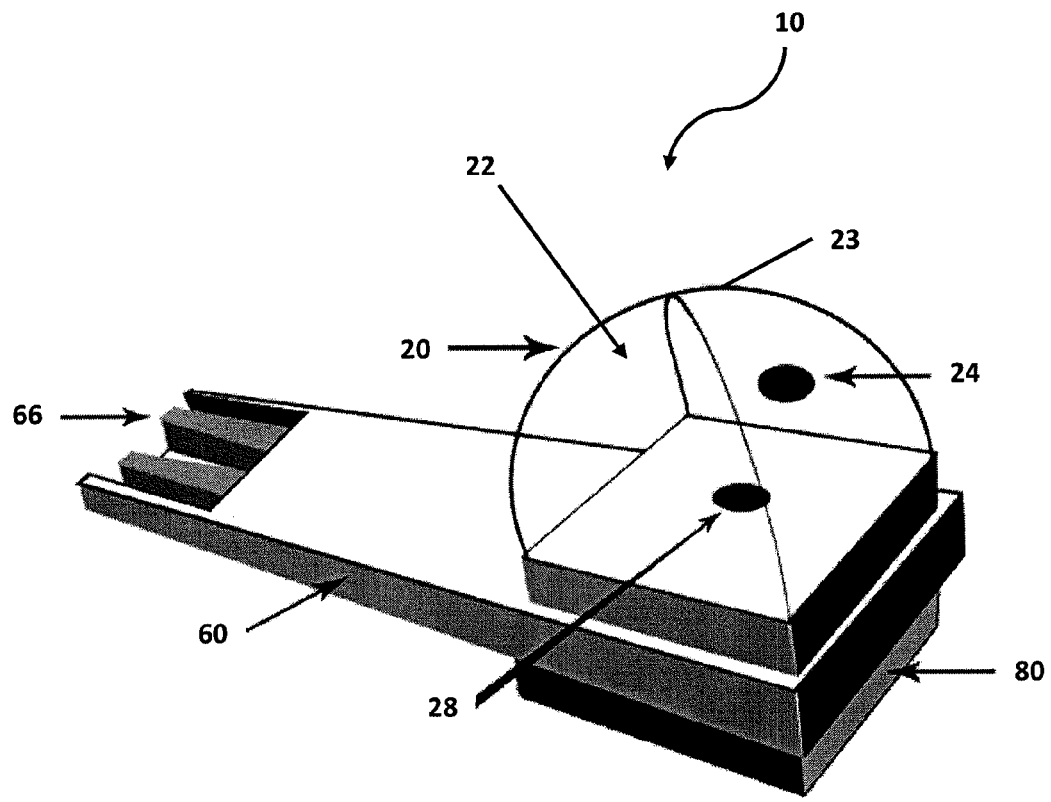
FIG. 2 illustrates a front view of an integrated needle and test strip assembly, showing an electrode system used to connect to a digital reader, a location for an uppermost flange of the needle, and a compartment created by a differential pressure chamber, in accordance with certain aspects of the present invention.

In accordance with an aspect of the present invention and as shown in FIGS. 1 and 2, the differential pressure chamber 20 may include a compartment 22 that may be rigid or may be deformable. The pressure chamber 20 may be pre-inflated with high pressure air, inert gas, or any other suitable fluid, and a fluid release mechanism 24, which may be a one-way or check valve, for example. The pressure chamber may alternately contain a vacuum. The compartment 22 may be formed to create a sealed, fluid protection barrier that may be transparent for the user to view a blood or interstitial fluid fill level in an embodiment where such filling is desirable, for example. The compartment 22 may be formed from a polymer or any other suitable material 23. The compartment 22 may be flexible, it may be inflatable, and it may be filled with a pressurized fluid having a higher than ambient room pressure, or placed under a vacuum in certain embodiments. A fluid protection plate 26 may be provided to serve as a mounting substrate for the compartment 22 in certain embodiments, and may include a duct 28 to provide communication between the inside of the compartment 22 and the needle flange 52. A portion of the duct 28 may also serve to assist in seating the uppermost needle flange 52 when the components of the integrated needle and test strip assembly 10 are assembled.

In accordance with an aspect of the present invention, one or more one-way or check valves (not shown) may be integrated into the aspiration needle/syringe apparatus with integrated test strip 10, at a predetermined location(s) between the distal end 54 of the needle 50 and the interior of the compartment 22. These one-way valves may ensure that the high-pressure gas in the compartment 22 may only escape via the fluid release mechanism 24, rather than through the distal end 54 of the needle 50. For example, a one-way valve may be integrated into the duct 28 in the fluid protection plate 26, onto the needle flange 52, or provided at any other location along the fluid path from an inlet at the distal end 54 of the needle 50 to an inlet into the interior of the compartment 22.

In embodiments, a fluid filter 30 may be situated between the differential pressure chamber 20 and the sensor strip 40, the filter 30 being configured to allow air or gas to pass while preventing any collected fluid from being drawn into the compartment 22. The filter 30 may also provide a method to hold the collected patient fluid on a chemical reaction layer of the sensor strip 40.

As shown in FIG. 1, the analyte reaction assembly 60 may be constructed by forming a sandwich of several layers of electrically insulating substrates. For example, a first insulating substrate 62 may contain a supply port 64 to hold the needle 50 inline and anchored within the analyte reaction assembly 60. Two or more electrodes 66 may be glued, affixed or printed onto the insulating substrate 62. An additional insulating layer 70 may be adhered or affixed to the first insulating substrate 62 so that the electrodes 66 may be effectively sandwiched between the two layers. This second insulating layer 70 may contain a cutout portion 72 that allows at least a portion of each of the electrodes 66 to remain exposed for mating the analyte reaction assembly 60 to an analyte meter. That is, the electrodes 66 may extend from the analyte reaction assembly 60 out of the integrated needle and test strip assembly 10 and may be attached to an analyte meter, which may be designed to accept the integrated needle and test strip assembly 10 of the present invention. The second insulating layer 70 may also contain a cutout section which defines an analyte reaction region 74, configured to hold the sensor strip 40 when the integrated needle and test strip assembly 10 is assembled. At least a portion of the electrodes 66 may be exposed at the analyte reaction region 74.

In embodiments, the sensor strip 40 may contain reaction reagents that allow the integrated needle and test strip assembly 10 to test the content of an analyte in the sample. Readout of the results of such a test may be provided when the integrated needle and test strip assembly 10 is attached to an analyte meter. During use, the sample collected by the integrated needle and test strip assembly 10 may contain an analyte which becomes mixed with one or more reaction reagents in the sensor strip 40. The reaction reagent may dissolve in the sample solution (e.g. if the reagents exist in a dry state on the sensor strip) and/or become mixed with the sample solution (e.g. if the reagents exist in a liquid state on the sensor strip) allowing the analyte to become oxidized or reduced by the reaction reagent. The concentration of the analyte in the sample solution may be determined based on the electrical current produced by the oxidation/reduction reaction which is sensed at the electrodes 66. As such, measurement of various analytes in the sample is possible if a suitable corresponding reaction reagent is selected. For example, if the integrated needle and test strip assembly 10 is used to measure a glucose concentration in a patient's blood sample, at least one of the reaction reagents may be glucose oxidase or glucose dehydrogenase.

The analyte tested on the sensor strip 40 of the integrated needle and test strip assembly 10 may be a chemical compound or organic molecule such as, for example, a sugar, glucose, lactate, fructosamine, glutamine, a ketone, pyruvate, 3-hydroxybutyric acid, acetyl choline, cholesterol or peroxide. The analyte tested may be a protein or enzyme such as, for example, prostate-specific antigen, prothrombin, hemoglobin, myoglobin, albumin, troponin, C-reactive protein, amylase, alanine transaminase, aspartate transaminase, alkaline phosphatase or creatine kinase. The analyte tested may be a peptide such as, for example, brain natriuretic peptide (proBNP). The analyte tested may be a break-down product of metabolism such as, for example, creatinine, bilirubin or uric acid. Further, the analyte tested may be a hormone such as, for example, luteinizing hormone, chorionic gonadotropin or thyroid stimulating hormone. The analyte tested may be a drug, such as, for example, an antibiotic (e.g., gentamicin, vancomycin, and the like), digitoxin, digoxin, a drug of abuse (e.g., barbiturates, methadone, amphetamine and amphetamine analogues, propoxyphene, opiates, cocaine, tetrahydrocannabinol, benzodiazepines, phencyclidine, and the like), theophylline or warfarin. The analyte tested may be a virus or bacterium. The analyte tested may be a coagulate, such as from a blood sample when mixed with Thromboplastin or thrombin. In embodiments, the analyte tested may be glucose and a reaction reagent in the sensor strip may be glucose oxidase or glucose dehydrogenase.

In embodiments, the integrated needle and test strip assembly 10 may use photometric rather than electrochemical means to detect a signal indicative of an analyte concentration in the sample of patient's bodily fluid. The analyte in the sample may mix with reaction reagents on the sensor strip 40 or may remain unreacted (i.e. unchanged). The analyte reaction assembly 60 may thus be constructed without electrodes 66, but may instead provide a means for allowing the reacted or unreacted analyte on the sensor strip 40 to be analyzed or detected by an analyte meter. Detection may be by any photometric means known in the art such as, for example, a shift in wavelength, a change in reflectance, transmittance, absorbance, fluorescence, luminescence or phosphorescence. In embodiments, the analyte in the sample may mix with reaction reagents on the sensor strip 40 that cause a color change which may be readable by the user or patient. As such, results of an analyte test using the integrated needle and test strip assembly 10 may be determined directly without attachment to an analyte meter.

The integrated needle and test strip assembly 10 may be constructed by extending the needle 50 through the analyte reaction region 74 and the supply port 64 of the analyte reaction assembly 60 so that the distal end 54 of the needle 50 is held in place by, and protrudes from a lower surface of, the first insulating substrate 62. In this manner, the needle 50 may be configured to protrude a predetermined distance, accommodating varying needle lengths and gauges, such as needles having a protruding length of 0.2 mm to 1.0 mm and having a gauge of 25 to 35, for example. The sensor strip 40, which may be wholly composed of a reaction reagent chemical composition deposited into the analyte reaction region 74, for example, may form a test layer duct 42 designed to further stabilize the needle 50 and to seat the needle flange 52. Moreover, the analyte reaction region 74 of the second insulating layer 70 may be configured to not only hold the sensor strip 40, but to also allow direct communication between the analyte chemicals of the sensor strip 40 and the electrodes 66.

The needle 50 may thus be stabilized and mounted into the integrated test strip assembly 60 with the needle flange 52 situated in a manner to aspirate fluid onto the analyte chemical layer of the contained sensor strip 40. The fluid filter 30 and the differential pressure chamber 20 may then be mounted, such as by adhesive or heat seal, for example, onto the analyte reaction assembly 60. The cutout section 74 may be configured, for example, to seat the differential pressure chamber 20 with the sensor strip 40 effectively sealed between the fluid protection plate 26 of the differential pressure chamber 20 at the top and the electrodes/first insulating substrate 62 at the bottom.

In accordance with an aspect of the present invention, the differential pressure chamber 20 may be formed without the fluid protection plate 26, for example, by forming the compartment 22 to have the material 23 attached directly to the walls of the cutout section 74, or otherwise formed to be in substantially direct communication with the sensor strip 40, regardless of whether separated by the fluid filter 30. The sensor strip 40 would thus be completely contained in the analyte reaction region 74 in a sealed environment, preventing contamination of the analyte chemical layer and ensuring a substantially aseptic environment for the testing of the patient's blood or interstitial fluid.

The needle guide and protection assembly 80 may be provided to protect the distal end 54 of the needle 50 during transport and handling while preventing contamination of the aseptically contained sensor strip 40. The assembly 80 may include, for example, a needle guide 82 and a protective needle cover 86. The needle guide 82 may be configured to have a needle duct 84. Further, in embodiments, the needle guide 82 may be composed of a deformable material, such as foam, that may compress when the integrated needle and test strip assembly 10 is pressed to the patient's skin.

The needle guide 82 may be further configured to have an adhesive coating on a bottom side (facing the protective needle cover) which may serve to hold the protective needle cover 86 in place prior to use of the integrated needle and test strip assembly 10. To ensure the assembly 10 has not been accessed prior to use, a tamper indicator may be included on the protective needle cover 86. For example, a perforation may be positioned over a seam formed at the edges of the protective needle cover 86, such as at an edge congruent with the needle guide 82. A ripped or torn perforation could then indicate that the assembly 10 has been opened and that the needle 50 may no longer be sterile. While a perforation is mentioned as a possible tamper indicator, any means for providing a tamper evident seal known in the art may be used and is within the scope of the present invention.

The adhesive coating on the needle guide 82 may also provide a means for holding the integrated needle and test strip assembly 10 in place during use on a patient. As mentioned previously, most current lancet systems use a mechanical spring loaded actuator to trigger the lancet's entry into the patient's skin. Movement and vibrations of the lancet, once actuated, have been shown to stimulate nerve sensors beneath the skin and cause pain for the patient. Further, such movement may allow the wound channel to collapse, thus reducing the ability to collect a sample. The adhesive coating on the needle guide 82 may allow the integrated needle and test strip assembly 10 to remain in place during sample collection, thus reducing any movement of the needle 50 once deployed within the patient's cutaneous or subcutaneous layer. Furthermore, the present integrated needle and test strip assembly 10 may simply be pressed into the patient's cutaneous or subcutaneous layer, for example the patient's fingertip, using another finger.

FIG. 2 illustrates a perspective view of the integrated needle and test strip assembly 10 as assembled. The compartment 22 is shown in a state in which it may be filled with high pressure air or gas or evacuated, for example. The analyte reaction assembly 60 in this embodiment is sandwiched between the differential pressure chamber 20 and the needle guide and protection assembly 80. The sensor strip 40 is self-contained in the interior of the integrated needle and test strip assembly 10 and may be visible, for example, by using transparent materials for aspects of the apparatus, including, for example, the components of the differential pressure chamber 20. The electrodes 66 are exposed and ready for easy and efficient connection of the integrated needle and test strip assembly 10 to an analyte meter or suitable device for reading the results of the chemical reaction that will occur when the sample of bodily fluid is aspirated onto the sensor strip 40.

In accordance with an aspect of the present invention, a patient's blood or interstitial fluid is collected cutaneously or subcutaneously and does not need to propagate to the surface of the skin. Through the use of the needle 50 disclosed herein, the fluid sample is collected and aspirated directly onto the sensor strip 40 of the analyte reaction assembly 60, controlling the flow of the bodily fluid and sealing the pressure differential to the wound after a sufficient, predetermined amount of bodily fluid is collected. By the use of a controlled vacuum and/or differential pressure chamber 20, the patient may not observe any bodily fluid on the surface of the skin once the fluid has been collected. Thus, the discomfort to the patient will be minimized and the possibility of dealing with blood or interstitial fluid spillage is reduced.

The ability to collect a predetermined amount of bodily fluid cutaneously or subcutaneously provides a myriad of advantages to the testing process as the chemical reaction can be contained with little opportunity of contamination or misapplication of fluid sample onto the sensor strip 40. The disclosed integrated needle and test strip assembly 10 allows for the reading of an analyte concentration in either a photometric or electrochemical manner, for example, hence providing a flexibility to use existing test strip readers and simply adapting the disclosed assembly 10 to commercially available readers rather than creating a new reader or developing a differently shaped test strip.

In embodiments, the integrated needle and test strip assembly 10 may be made to visually appear substantially similar to current test strip designs, for example, thereby providing a sense of continuity to patients that already use a certain brand or style of test strip. The disclosed integrated needle and test strip assembly 10 may simplify the patient's daily fluid collection process while enhancing the accuracy of that process.

Figure 3:
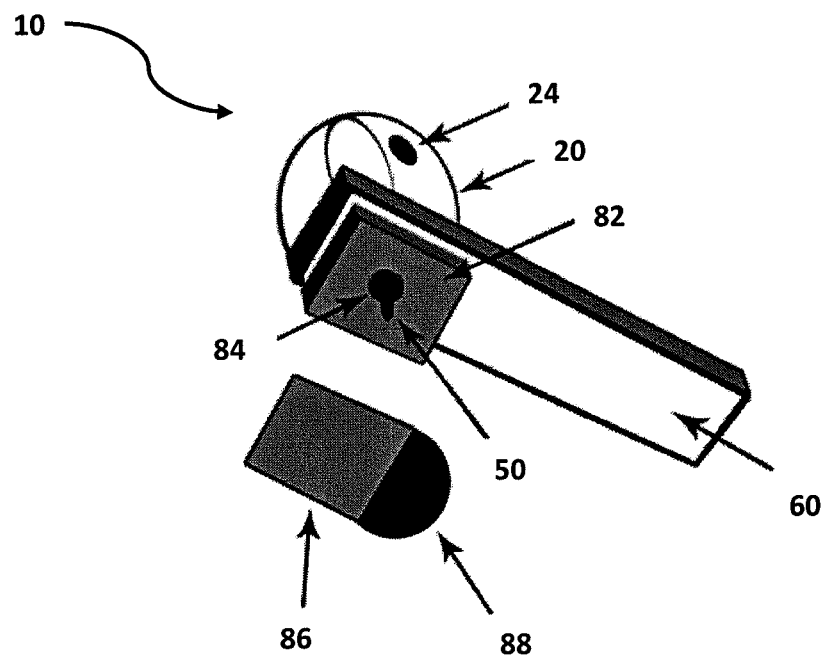
FIG. 3 illustrates a bottom view of an integrated needle and test strip assembly having a protective layer removed to expose the needle centered within a needle guide, in accordance with certain aspects of the present invention.

FIG. 3 illustrates a bottom perspective view of the integrated needle and test strip assembly 10. The needle 50 may extend from the needle duct 84 of the needle guide 82. The protective needle cover 86, which may be adhesively applied, for example, may protect the exposed portion of the needle 50 and further prevent contaminants from entering into the interior of the integrated needle and test strip assembly 10. A finger positioning flap 88 may be provided to allow the protective needle cover 86 to be easily and ergonomically detached from the needle guide 82. This view also shows the differential pressure chamber 20 and the fluid release mechanism 24.

Figure 4:
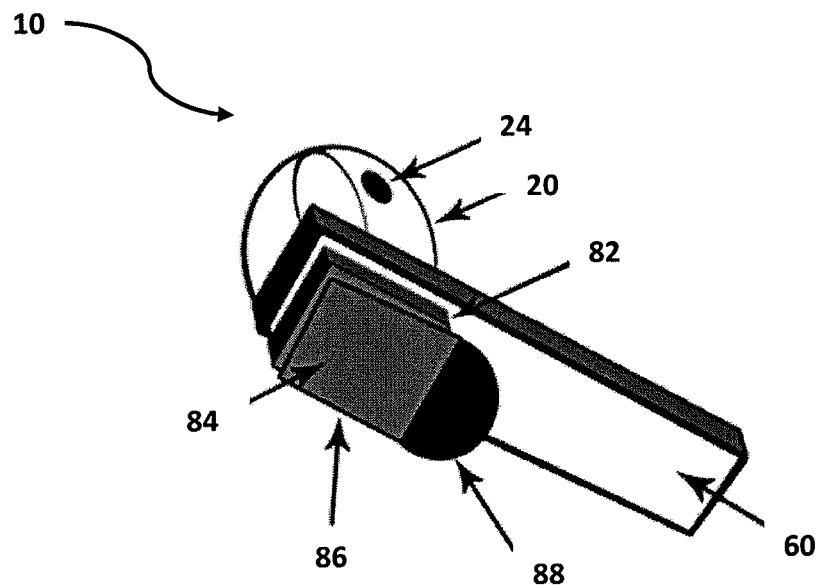
FIG. 4 illustrates a bottom view of an integrated needle and test strip assembly having the protective layer attached to thereby protect a user from accidental sticks/pricks, provide for sterile protection of the needle, and for use in discarding, in accordance with certain aspects of the present invention.

FIG. 4 illustrates a bottom perspective view of the integrated needle and test strip assembly 10, wherein the protective needle cover 86 is affixed onto the needle guide 82 to provide a protective barrier. As shown, the integrated needle and test strip assembly 10 is configured so the user is not susceptible to sticks or pricks from the needle 50 when the protective needle cover 86 is affixed. In addition, the integrated needle and test strip assembly 10 may be more readily packaged, stored, shipped, and handled without the threat of damage or tearing as a result of the needle 50.

Figure 5:
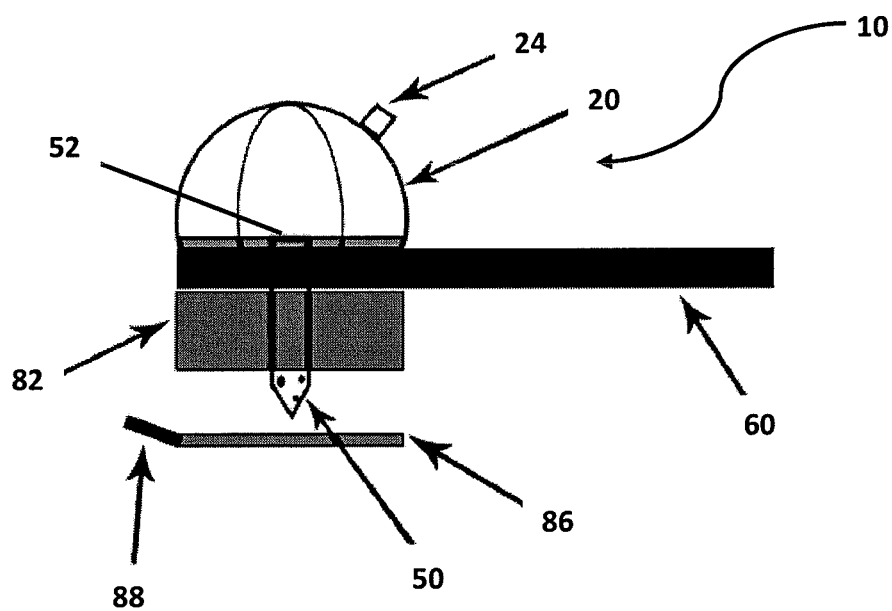
FIG. 5 illustrates a side view of an integrated needle and test strip assembly having the protective layer removed to thereby expose the needle, in accordance with certain aspects of the present invention.

FIG. 5 shows the integrated needle and test strip assembly 10 from a side view perspective. The distal end 54 of the needle 50 protrudes from the needle guide 82. The protective needle cover 86 is shown in the removed position. The differential pressure chamber 20 is shown and the fluid release mechanism 24 is also indicated. Any fluid collected by the needle 50 may be deposited onto the sensor strip 40 of the analyte reaction assembly 60 by virtue of the predetermined positioning of the uppermost needle flange 52. For example, the needle 50 may be positioned so that the blood or interstitial fluid is released from the opening of the needle flange 52 onto an upper layer of the sensor strip 40, or the opening of the needle flange 52 may be situated slightly lower into the test layer duct 42 (see FIG. 1) to release the blood or interstitial fluid into a more central region or even onto a lower surface of the analyte chemical layer of the sensor strip 40.

Figure 6:
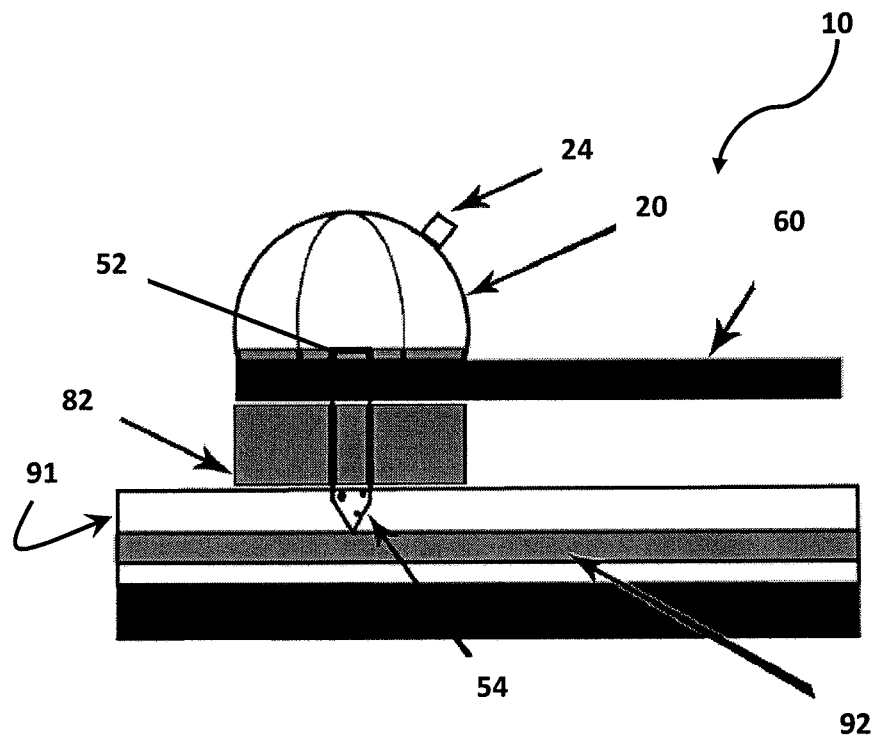
FIG. 6 illustrates a side view of an integrated needle and test strip assembly in a state of use after the apparatus contacts the patient's skin and begins to penetrate the dermal layer, but before complete depth is achieved, to illuminate a function of the needle guide, in accordance with certain aspects of the present invention.

FIG. 6 shows the integrated needle and test strip assembly 10 from a side view perspective, showing the patient's skin 91 penetrated by the distal end 54 of the needle 50 with the needle guide 82 seated firmly against the surface of the skin and the differential pressure chamber 20 having not yet been engaged. The patient's blood or interstitial fluid 92 is shown within the skin 91 and the distal end 54 of the needle 50 has not penetrated deeply enough to collect a sample of the fluid 92. Without the user applying pressure to the differential pressure chamber 20, the needle 50 may not penetrate deeply enough to position the distal end 54 within the blood or interstitial fluid containing tissue.

Figure 7:
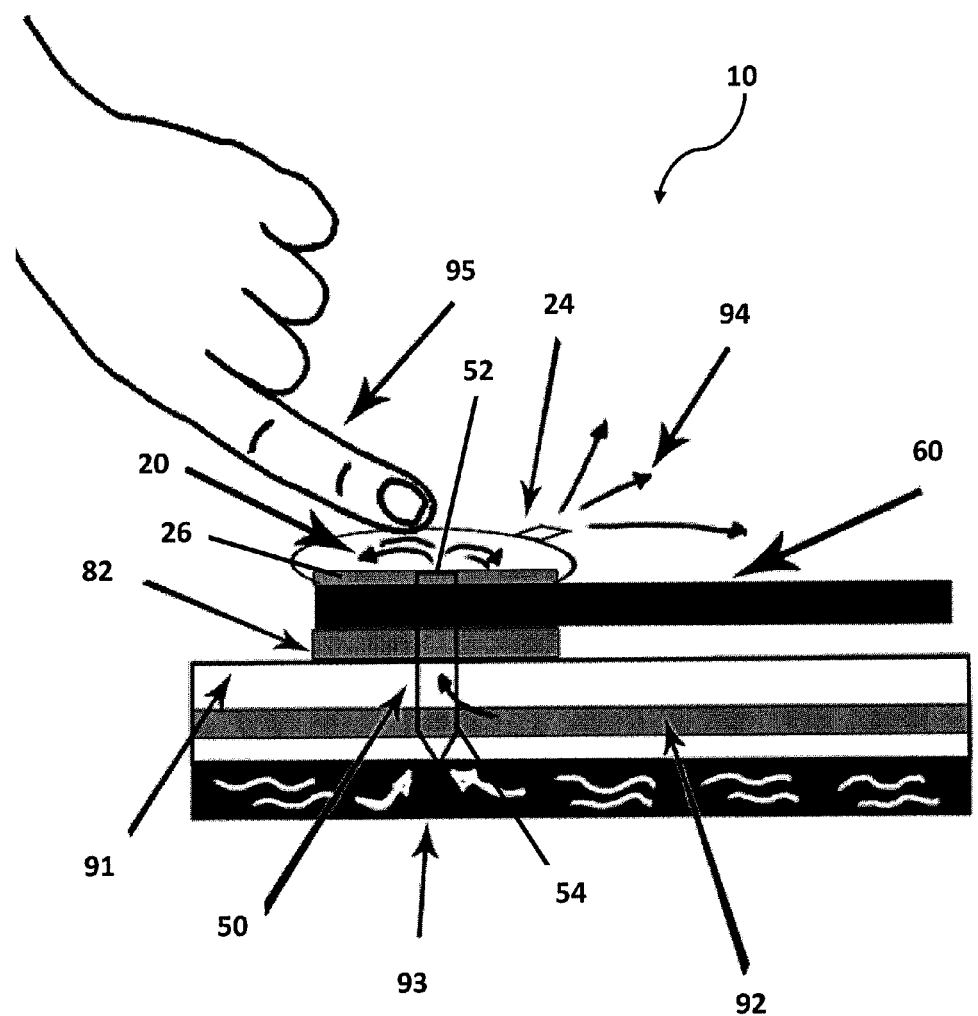
FIG. 7 illustrates a side view of an integrated needle and test strip assembly in a state of use during which the user applies pressure to the differential pressure chamber with full penetration of the needle in the patient's dermal layer to demonstrate aspiration of bodily fluid into the needle while being simultaneously deposited onto the sensor strip within the reaction region of the analyte reaction assembly, in accordance with certain aspects of the present invention.

FIG. 7 illustrates the integrated needle and test strip assembly 10 and the user 95 applying pressure to the differential pressure chamber 20 while the fluid release mechanism 24 releases the higher than room ambient pressure air or other gaseous fluid. This escaping fluid 94 causes a low pressure environment to be created in the needle 50, thereby aspirating the blood or interstitial fluid 92 from the blood containing tissue 93 through the distal end 54 of the needle 50 to the needle flange 52 for release onto the sensor strip 40. In another embodiment wherein the differential pressure chamber 20 is evacuated, actuation of the differential pressure chamber 20 also causes a low pressure environment to be created in the needle 50, thereby aspirating the blood or interstitial fluid 92 from the blood containing tissue 93 through the distal end 54 of the needle 50 to the needle flange 52 for release onto the sensor strip 40. The needle guide 82 may further be squeezed under the pressure applied by the user, allowing the needle 50 to penetrate the skin at a substantially perpendicular angle, for example, to the integrated needle and test strip assembly 10.

In accordance with an aspect of the present invention, the integrated needle and test strip assembly 10 may be configured with the compartment 22 of the differential pressure chamber 20 evacuated prior to use such that a vacuum exists within the compartment 22. In embodiments, the compartment 22 may be comprised of a hard plastic material, for example, or any suitable material for maintaining a vacuum without collapsing. A control valve (not shown), for example, may be situated between the needle 50 and the inlet into the interior of the compartment 22. Thus, upon insertion of the needle 50, the user may open the control valve or otherwise actuate the integrated needle and test strip assembly 10 so that the difference in pressure between (1) the vacuum in the compartment 22 and (2) the volume of blood or interstitial fluid 91 will draw the blood or interstitial fluid 91 through the needle 50 to the sensor strip 40.

Figure 8:
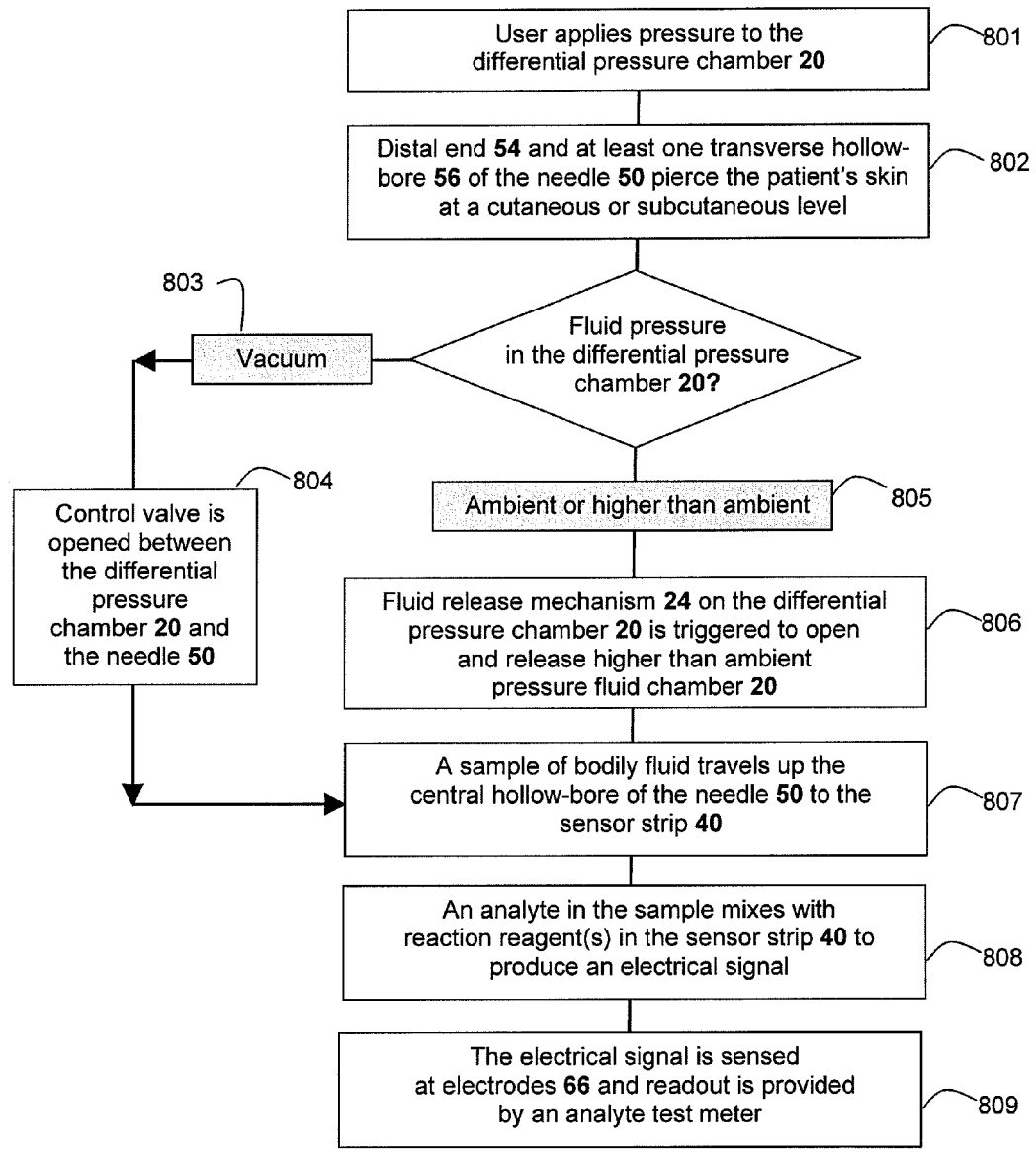
FIG. 8 depicts an exemplary flow diagram of a method of use of an integrated needle and test strip assembly, in accordance with certain aspects of the present invention.

FIG. 8 depicts an exemplary flow diagram describing one embodiment of a method of the present invention. At step 801, the user applies pressure to the differential pressure chamber 20 of the integrated needle and test strip assembly 10. The distal end 54 of the needle 50 and at least one transverse hollow-bore or orifice 56 pierce the patient's skin at a cutaneous or subcutaneous level, as shown at step 802. If the differential pressure chamber 20 contains a fluid, such as a gas, that is at ambient or higher than ambient pressure (step 805), the fluid release mechanism 24 on the compartment 22 of the differential pressure chamber 20 may open, as shown at step 806. The ambient or higher than ambient pressure fluid may be released. As the user applies additional pressure to the differential pressure chamber 20, a vacuum may form in the compartment 22. The vacuum may then draw a sample of bodily fluid in through the distal end 54 and at least one orifice 56 of the needle 50 and up the central hollow-bore to the upper flange 52, where the sample may flow onto the sensor strip 40, as shown at step 807. The fluid filter 30, which may be located at a position above the sensor strip 40, allows gas but not fluid to pass to the compartment 22 of the differential pressure chamber 20. As such, the fluid filter 30 may capture excess bodily fluid that is collected and may further aid in reaction on the sensor strip 40 by holding a reservoir of sample in contact with the sensor strip 40. Once the sample of bodily fluid has become introduced to the sensor strip 40, an analyte in the sample may react with reagents on the sensor strip 40, as shown at step 808. The reaction on the sensor strip may produce an electrical signal that is detected by the electrode(s) 66, as shown at step 809. This signal may be read by an analyte test meter.

If the differential pressure chamber 20 is evacuated so that the compartment 22 contains lower than ambient pressure such as a vacuum (step 803), a control valve may be triggered to open by the user (step 804). The control valve may be at any position along the fluid path between the distal end 54 of the needle 50 and the differential pressure chamber 20. The control valve may hold the vacuum in the compartment 22 until opened by the user, at which point the vacuum in the compartment 22 may be in fluid communication with the sample of bodily fluid. The vacuum may draw a sample of bodily fluid in through the distal end 54 and at least one orifice 56 of the needle 50 and up the central hollow-bore to the upper flange 52, where the sample may flow onto the sensor strip 40, as shown at step 807. Subsequent steps are as described above.

In embodiments, the signal produced at step 808 may be photometric rather than electrochemical. The analyte reaction assembly 60 may thus be constructed without electrodes 66, but may instead provide a means for allowing the reacted or unreacted analyte on the sensor strip 40 to be analyzed or detected by an analyte meter. Accordingly, detection of the signal may be by spectrophotometric means rather than at electrodes, as shown in step 809. In alternative embodiments, the analyte in the sample may mix with reaction reagents on the sensor strip 40 that cause a color change which may be readable by the user or patient. As such, the signal produced at step 808 may be determined directly without attachment to an analyte meter.

Performing the above-discussed steps greatly improves the ease of sample collection and reduces the pain a patient experiences. In prior art systems it can be difficult for patients, especially for patients with limited hand dexterity, such as the elderly, to collect a sample of bodily fluid. In a typical procedure, the patient first creates an incision in the skin by lancing the skin with the lancet. Once a sufficient amount of fluid collects as a droplet on the skin, the patient has to position a test strip over the incision site such that the test strip contacts and absorbs a sufficient amount of the fluid for analysis. Usually, these droplets of fluid are quite small, and patients, especially ones with poor hand motor control, may experience great difficulty in positioning the test strip so as to collect an adequate sample from the droplet. As should be appreciated, a patient can become quickly frustrated by this procedure and, consequently, they may perform the test less often or may even quit testing altogether. The integrated needle and test strip assembly 10 of the present invention solves these problems.

In accordance with an aspect of the present invention, the sample may be drawn from the distal end 54 of the needle 50 to the needle flange 52 by capillary action. As such, no differential pressure may be needed in the differential pressure chamber 20, and a needle deployment positioning device may replace the differential pressure chamber 20. As shown in FIG. 7, the needle 50 may be pushed into the skin 91 to come into contact with blood or interstitial fluid 92, and the fluid may pass through the distal end 54 of the needle 50 and the orifice(s) 56 to the sensor strip 40 by capillary action. The needle deployment positioning device, which may be in the same location as the differential pressure chamber 20, may be a region visually marked or physically different to guide the user to apply force to that region. Once force is applied, the needle guide 82 may be squeezed under the pressure applied by the user, allowing the needle 50 to penetrate the skin at a substantially perpendicular angle, for example, to the integrated needle and test strip assembly 10.

Figure 9:
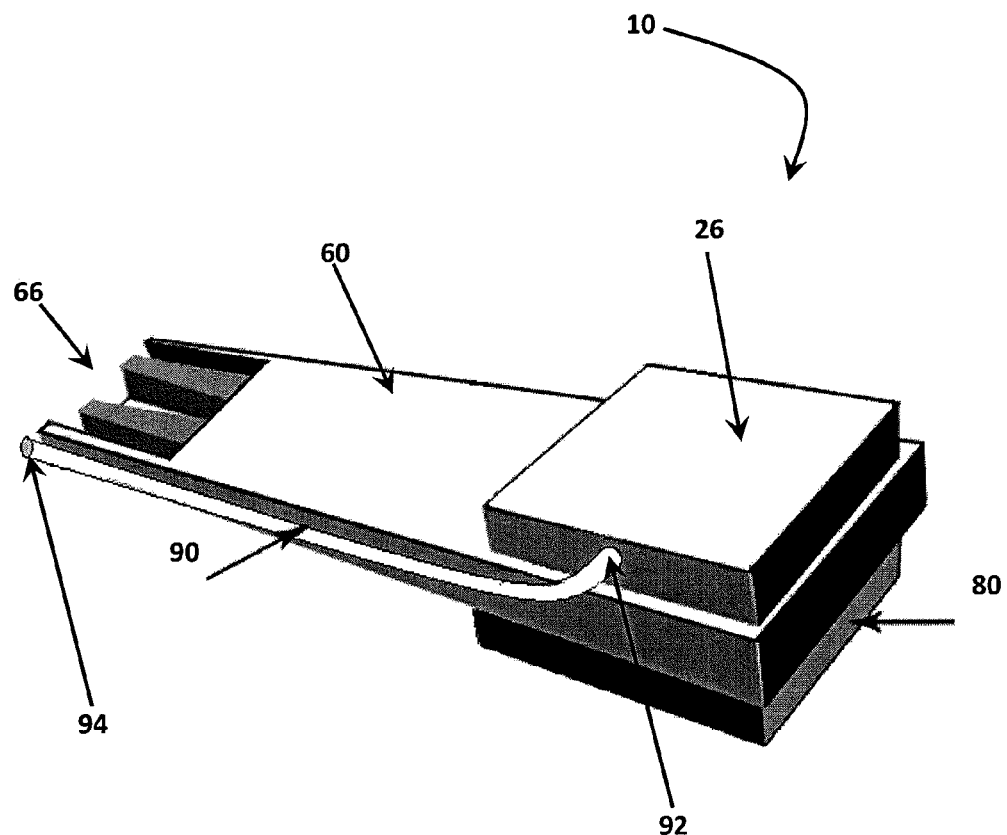
FIG. 9 illustrates a front view of an integrated needle and test strip assembly, showing a conduit used to connect to a differential pressure device on a digital analyte reader, and a location for a duct in a fluid protection plate, in accordance with certain aspects of the present invention.
Figure 10:
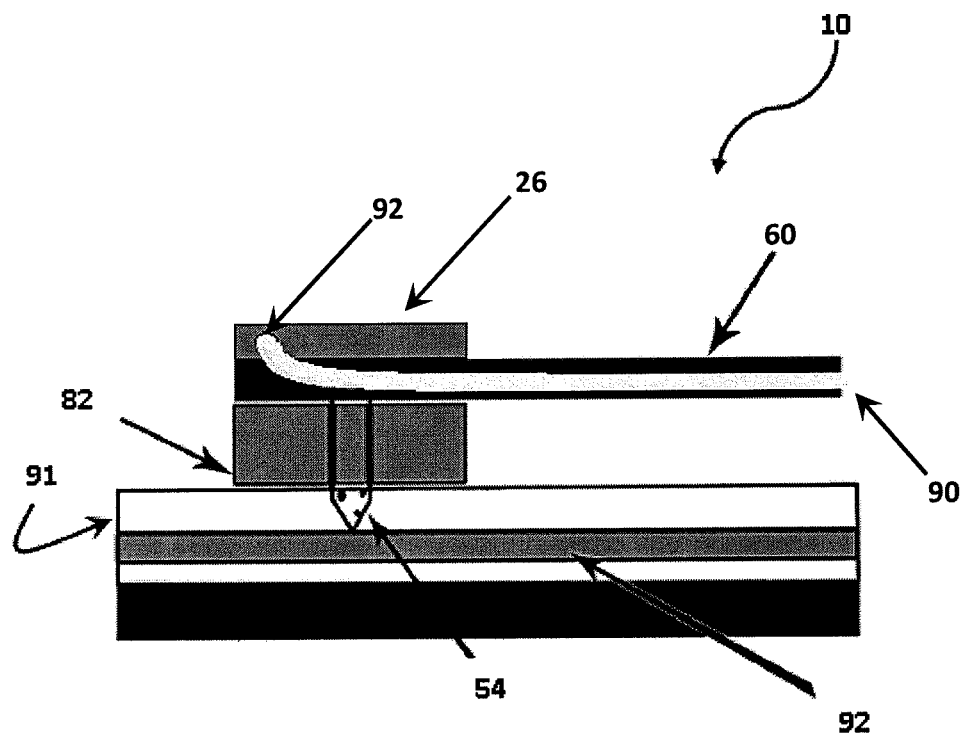
FIG. 10 illustrates a side view of an integrated needle and test strip assembly in a state of use after the apparatus contacts the patient's skin and begins to penetrate the dermal layer, but before complete depth is achieved, to illuminate a function of the needle guide and location of the conduit used to connect to a differential pressure device on a digital analyte reader, in accordance with certain aspects of the present invention.

In accordance with an aspect of the present invention, further embodiments of the integrated needle and test strip assembly of the present invention are shown in FIGS. 9 and 10 generally designated by the reference numeral 10. The integrated needle and test strip assembly 10 may be configured so that the differential pressure required to aspirate a sample may be provided by a syringe or vacuum pump. In embodiments, the syringe or vacuum pump may be resident on the integrated needle and test strip assembly 10 or may be resident on an analyte test meter with which the integrated needle and test strip assembly 10 docks. In the case of a syringe, if the syringe is pulled out to 65 mm, assuming atmospheric pressure of 1 atm, the pressure in the system may be calculated to drop to 0.017 atm (about 0.25 psia or 13 torr). A calculated force on the syringe to achieve this drop in pressure would be about 0.3 lbs. Such a force would be easily attainable by either the analyte test meter or the user or patient, and the reduced pressure in the system would readily aspirate a sample of bodily fluid through the distal end 54 of the needle 50 and the orifice(s) 56 to the sensor strip 40.

As shown in FIG. 9, embodiments of the integrated needle and test strip assembly 10 may comprise a catheter or conduit 90 which may exit a side of the fluid protection plate 26 and provide a means for attachment to the analyte test meter. As such, the distal end 54 of the needle 50 may be in fluid communication with a differential pressure apparatus residing on the analyte test meter. The differential pressure apparatus may be a syringe or vacuum pump, as discussed above. In such an embodiment, the differential pressure chamber 20 may not be included in the integrated needle and test strip assembly 10. Rather, a needle deployment positioning device may be included which may be in the same location as the differential pressure chamber 20, and may be a region visually marked or physically different to guide the user to apply force to that region. The fluid protection plate 26 may serve as a mounting substrate for the conduit 90 in certain embodiments, and may include a duct or port 92 to provide fluid communication between the uppermost flange 52 of the needle 50 and the conduit 90.

In embodiments, the fluid filter 30 may be situated between the fluid protection plate 26 and the sensor strip 40, the fluid filter 30 being configured to allow air or gas to pass while preventing any collected fluid from being drawn into the conduit 90 or the analyte test meter. The conduit 90 may be positioned to exit the fluid protection plate 26 at any point that does not interfere with the needle deployment positioning device or a user's ability to apply force to the needle deployment positioning device. While the conduit 90 is shown to exit port 92 at a center point on a side of the fluid protection plate 26 in FIG. 9, this is merely for illustrative purposes and does not limit the present invention in any way.

In embodiments, the conduit 90 may facilitate connection to a differential pressure device on the analyte test meter via a conduit connector end 94. The conduit connector end 94 may be a male or female connector, and may be interchangeable to provide connection to a variety of analyte test meters.

FIG. 10 shows the integrated needle and test strip assembly 10 from a side view perspective, showing the patient's skin 91 penetrated by the distal end 54 of the needle 50 with the needle guide 82 seated firmly against the surface of the skin. The conduit 90 is shown to exit a side of the fluid protection plate 26 at port 92. As discussed above, while the conduit 90 is shown to exit port 92 at an end point on a side of the fluid protection plate 26, this is merely for illustrative purposes and does not limit the present invention in any way. Furthermore, while the conduit connector end 94 is shown to be adjacent to the electrodes 66, this is merely for illustrative purposes and does not limit the present invention in any way. The conduit 90 may take any path along the integrated needle and test strip assembly 10 that may allow for connection to the analyte test meter.

Also shown in FIG. 10 is the patient's blood or interstitial fluid 92 within the skin 91 and the distal end 54 of the needle 50. The needle 50 may not have penetrated deeply enough to collect a sample of the fluid 92 until the user applies pressure to the needle deployment positioning device or a top portion of the fluid protection plate 26. When pressure is applied by the user, the needle 50 may penetrate deeply enough to position the distal end 54 and at least one orifice 56 within the blood or interstitial fluid containing tissue. The differential pressure device on the analyte meter may then aspirate a sample up through the distal end 54 and at least one orifice 56 of the needle 50 onto the sensor strip 40.

In accordance with an aspect of the present invention, the needle guide 82 may be an interchangeable and configurable component. In embodiments, the integrated needle and test strip assembly 10 may be configured with any one of a variety of needle guides 82, wherein each needle guide 82 may have a different thickness, for example. Accordingly, without changing the length of the needle 50, the depth to which the needle 50 may penetrate the skin 91 can be adjusted by simply changing to a different needle guide 82, or selecting an integrated needle and test strip assembly 10 having the desired thickness of needle guide 82 already mounted. In this manner, it may be extremely easy to account for the many variations of a patient, such as age and/or skin thickness.

In accordance with various aspects of the present invention discussed herein, an embodiment of the integrated needle and test strip assembly may comprise a needle and a test strip. The needle 50 may have an upper flange 52, a distal end 54, a central hollow-bore extending through at least a portion of the needle 50, and at least one transverse hollow-bore 56 near the distal end 54 which is in fluid communication with the central bore. The test strip, which may be in fluid communication with the upper flange 52 of the needle 50, may include a combination of electrical, chemical, and/or optical components configured to provide a response indicative of the presence or concentration of the analyte to be measured. The test strip may include a sensor strip 40 and an analyte reaction assembly 60 as described herein. In alternative embodiments, the test strip may be designed and manufactured in a manner much the same as test strips currently on the market, wherein the needle would be located in a position which would allow the sample to come into contact with a reaction region on the test strip. In embodiments, the sample may be drawn up through the central bore of the needle 50 by capillary action, or by a vacuum created by a differential pressure chamber 20, or through a conduit 90 or catheter which allows fluid communication with a differential pressure apparatus residing on an analyte test meter.

Although described herein with reference to an aspirating needle for withdrawing a discrete amount of blood or interstitial fluid for testing, it will be readily apparent to one of ordinary skill in the art to recognize the potential of using the integrated needle and test strip assembly 10 as a syringe. By changing the direction of the one-way valves, for example, the direction of fluid flow may easily be reversed. By prefilling the compartment 22 with a medication, for example, the integrated needle and test strip assembly 10 could be used to inject the medication into a patient subcutaneously, for example. The sensor strip 40 may be removed in such an embodiment.

The previous description is provided to enable any person skilled in the art to practice the various exemplary implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

Embodiments of the integrated needle and test strip assembly of the present invention may be configured to have similar dimensions and electrode placement as products currently on the market. Further, embodiments of the present invention may be designed to look very similar to currently marketed products. As such, a product of the present invention may allow greater user familiarity and require less modification of the manufacturing process, which may be advantageous in the market.

It should be noted that products described in the prior art are generally much larger in size and cumbersome to use because of the need for syringe operation or due to the inclusion of a mechanical lancet actuator. As such, many prior art products can only be used at alternate test sites rather than at the fingertip. Still yet other products require actuating devices to engage the needle (rather than no actuator at all), use of multiple needles and/or incorporate large fluid reservoirs for large samples. Embodiments of the integrated needle and test strip assembly described herein overcome these drawbacks. While some prior art products have incorporated the use of micro-needles, which may cause less pain, these products require more time for sample collection. As such, consumers are likely to find the longer sample collection times with micro-needles to be unacceptable and may perform the test less often or may even quit testing altogether.

While specific embodiments of the invention have been described in detail, it should be appreciated by those skilled in the art that various modifications and alternations and applications could be developed in light of the overall teachings of the disclosure. Accordingly, the particular arrangements, systems, apparatuses, and methods disclosed are meant to be illustrative only and not limiting as to the scope of the invention.

What is claimed is:

1. A needle assembly for aspiration of a sample, comprising:
a needle having an upper flange, a distal end, a central hollow-bore extending through at least a portion of the needle, and at least one transverse hollow-bore in fluid communication with the central bore;
a differential pressure chamber having at least one port in fluid communication with the central hollow-bore of the needle;
a needle guide having at least one port for passage of the needle, wherein the needle guide has an adhesive thereon and adjacent to the needle to impede horizontal and vertical movement of the needle during use;
a sensor strip containing at least one reaction reagent for determining a concentration of at least one analyte in the sample, the sensor strip disposed between the differential pressure chamber and the needle guide, the sensor strip having at least one port for passage of the upper flange of the needle;
a fluid filter permeable to gas but not fluids disposed between the sensor strip and the differential pressure chamber; and
an analyte reaction assembly disposed between the fluid filter and the needle guide and configured to contain the sensor strip within a reaction region, the analyte reaction assembly comprising:
an insulating substrate having an electrical terminal at a first end;
a first conductor disposed on the insulating substrate extending from the electrical terminal to the sensor strip;
a second conductor disposed on the insulating substrate extending from the electrical terminal to the sensor strip; and
an insulating layer disposed on the insulating substrate, first conductor, and second conductor.

2. The needle assembly of claim 1, wherein the differential pressure chamber is a compartment filled with a pressurized fluid and has at least one check valve, and whereby ejection of the pressurized fluid from the compartment through the check valve triggers a negative pressure which aspirates the sample through the needle onto the sensor strip.

3. The needle assembly of claim 2, wherein the pressurized fluid is a pressurized gas.

4. The needle assembly of claim 1, wherein the differential pressure chamber includes one of a syringe and a mechanical vacuum.

5. The needle assembly of claim 1, further comprising:
a check valve in fluid communication with the needle and the differential pressure chamber, the check valve allowing fluid to flow in a single direction between the needle and the differential pressure chamber.

6. The needle assembly of claim 1, further comprising:
a protective needle cover removably disposed over the needle guide adhesive, the protective needle cover maintaining a sterile environment for the needle, reaction region of the analyte reaction assembly, sensor strip and needle guide.

7. The needle assembly of claim 1, wherein the needle guide has a thickness that affects the depth of penetration of the needle during use.

8. The needle assembly of claim 1, wherein the sample comprises blood or dermal interstitial fluid.

9. The needle assembly of claim 1, wherein the needle is about 0.2 mm to 1.0 mm in length and about 25 gauge to 35 gauge in diameter.

10. The needle assembly of claim 1, wherein the volume of the sample is about 0.3 microliters to about 30 microliters.

11. The needle assembly of claim 1, wherein the analyte in the sample is at least one of glucose, lactate, fructosamine, glutamine, 3-hydroxybutyric acid, acetyl choline, amylase, bilirubin, alanine transaminase, aspartate transaminase, alkaline phosphatase, luteinizing hormone, chorionic gonadotropin, creatine kinase, creatinine, hemoglobin, myoglobin, albumin, troponin, cholesterol, a coagulate, C-reactive protein, brain natriuretic peptide (BNP), proBNP, uric acid, pyruvate, a hormone, a sugar, a ketone, peroxide, prostate-specific antigen, prothrombin, thyroid stimulating hormone, an antibiotic, a drug, a bacterium and a virus.

12. The needle assembly of claim 1, wherein a reaction reagent in the sensor strip is at least one of glucose oxidase and glucose dehydrogenase.

13. The needle assembly of claim 1, wherein the insulating substrate includes a void passing therethrough and wherein the sensor strip is disposed in the void.

14. The needle assembly of claim 1, wherein the differential pressure chamber comprises a compartment that is flexible and inflatable.

15. A needle assembly for aspiration of a sample, comprising:
   a needle having an upper flange, a distal end, a central hollow-bore extending through at least a portion of the needle, and at least one transverse hollow-bore in fluid communication with the central bore;
   a conduit to connect to a differential pressure device, the conduit in fluid communication with the needle;
   a needle guide having at least one port for passage of the needle, wherein the needle guide has an adhesive thereon and adjacent to the needle to impede horizontal and vertical movement of the needle during use;
   a sensor strip containing at least one reaction reagent for determining a concentration of at least one analyte in the sample, the sensor strip having at least one port for passage of the upper flange of the needle;
   a fluid filter permeable to gas but not fluids, the fluid filter adjacent to the sensor strip; and
   an analyte reaction assembly disposed between the fluid filter and the needle guide and configured to contain the sensor strip within a reaction region, the analyte reaction assembly comprising:
      an insulating substrate having an electrical terminal at a first end;
      a first conductor disposed on the insulating substrate extending from the electrical terminal to the sensor strip;
      a second conductor disposed on the insulating substrate extending from the electrical terminal to the sensor strip; and
      an insulating layer disposed on the insulating substrate, first conductor, and second conductor.

16. The needle assembly of claim 15, further comprising a fluid protection plate including a port, the port to provide fluid communication between the upper flange of the needle and the conduit.

* * * * *